US010539002B2

(12) United States Patent
Ye

(10) Patent No.: US 10,539,002 B2
(45) Date of Patent: Jan. 21, 2020

(54) IN-LINE VISCOMETER FOR MEASURING THE VISCOSITY OF DRILLING FLUIDS

(71) Applicant: Halliburton Energy Services, Inc., Houston, TX (US)

(72) Inventor: Xiangnan Ye, Cypress, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 436 days.

(21) Appl. No.: 14/911,501

(22) PCT Filed: May 1, 2015

(86) PCT No.: PCT/US2015/028786
§ 371 (c)(1),
(2) Date: Feb. 11, 2016

(87) PCT Pub. No.: WO2016/178650
PCT Pub. Date: Nov. 10, 2016

(65) Prior Publication Data
US 2017/0276584 A1    Sep. 28, 2017

(51) Int. Cl.
*E21B 47/00* (2012.01)
*E21B 21/06* (2006.01)
(Continued)

(52) U.S. Cl.
CPC .............. *E21B 47/00* (2013.01); *E21B 21/06* (2013.01); *E21B 47/06* (2013.01); *G01N 11/08* (2013.01); *E21B 21/067* (2013.01); *E21B 43/26* (2013.01)

(58) Field of Classification Search
CPC .. E21B 2049/085; E21B 21/067; E21B 43/26; E21B 47/10; E21B 21/06;
(Continued)

(56) References Cited

U.S. PATENT DOCUMENTS 4,726,219 A  *  2/1988  Pearson ................... E21B 21/01
                                                                73/152.39
5,042,296 A  *  8/1991  Burgess ................... E21B 21/08
                                                                73/152.19

(Continued)

OTHER PUBLICATIONS

Journal of Polymer Science 28: 619-622 (1958), Correlation of dynamic and steady flow viscosities.
(Continued)

*Primary Examiner* — Robert E Fuller
*Assistant Examiner* — Christopher J Sebesta
(74) *Attorney, Agent, or Firm* — Tenley Krueger; C. Tumey Law Group PLLC

(57) ABSTRACT

In-line viscosity measurement systems and related methods may be useful in measuring the viscosity of a fluid in a flow path and, more specifically, in-line measuring the viscosity of a drilling fluid when integrated with drilling systems. For example, a method may include drilling a wellbore penetrating a subterranean formation while circulating a drilling fluid through the wellbore; measuring the viscosity of the drilling fluid with an in-line viscometer system after the drilling fluid has circulated through the wellbore, the in-line viscometer systems comprising either: (1) a two coaxial cylinder configuration, (2) a parallel plates configuration, or (3) a combination thereof positioned to allow for the drilling fluid to flow between the coaxial cylinders or parallel plates.

12 Claims, 4 Drawing Sheets

(51) Int. Cl.
*G01N 11/08* (2006.01)
*E21B 47/06* (2012.01)
*E21B 43/26* (2006.01)

(58) Field of Classification Search
CPC ......... E21B 47/00; E21B 47/06; G01N 11/08; G01N 33/0047; G01N 33/2823
USPC ..................... 75/152.19, 54.01, 54.37, 54.39
See application file for complete search history.

(56) References Cited

U.S. PATENT DOCUMENTS

| | | |
|---|---|---|
| 5,750,884 A | 5/1998 | Field |
| 8,024,962 B2 | 9/2011 | Tonmukayakul et al. |
| 8,490,470 B1 * | 7/2013 | Kaukler ............... G01N 11/142 73/54.01 |
| RE44,943 E * | 6/2014 | O'Brien ................. G01N 11/04 137/10 |
| 8,794,051 B2 | 8/2014 | Morgan et al. |
| 2005/0087001 A1 | 4/2005 | Irani |
| 2007/0289739 A1 | 12/2007 | Cooper et al. |
| 2009/0090172 A1 | 4/2009 | Angelescu et al. |
| 2013/0025359 A1 | 1/2013 | Cartellieri et al. |
| 2013/0192360 A1 * | 8/2013 | Jamison ................. E21B 21/00 73/152.19 |
| 2013/0276518 A1 * | 10/2013 | Dagalakis ............. G01N 11/16 73/54.25 |

OTHER PUBLICATIONS

Rheol Acta 46: 111-121 (2006), The oscillatory squeeze flow rheometer: comprehensive theory and a new experimental facility.
International Search Report and Written Opinion for PCT/US2015/028786 dated Jan. 7, 2016.

* cited by examiner

IN-LINE VISCOMETER FOR MEASURING THE VISCOSITY OF DRILLING FLUIDS

BACKGROUND

The exemplary embodiments described herein relate to measuring the viscosity of drilling fluids.

Wellbore fluids often include a plurality of particles that impart specific properties (e.g., viscosity, mud weight (or density), and the like) and capabilities (e.g., wellbore strengthening) to the wellbore fluid. It should be understood that the terms "particle" and "particulate," as used in this disclosure, includes all known shapes of materials, including substantially spherical materials, fibrous materials, polygonal materials (such as cubic materials), and combinations thereof.

In drilling fluids, for example, weighting agents and viscosifiers can be used to produce drilling fluids with the desired viscosity, which affects the pumpability and equivalent circulating density ("ECD") of the drilling fluid. During drilling operations, for example, the ECD is often carefully monitored and controlled relative to the fracture gradient of the subterranean formation. Typically, the ECD during drilling is close to the fracture gradient without exceeding it. When the ECD exceeds the fracture gradient, a fracture may form in the subterranean formation and drilling fluid may be lost into the subterranean formation (often referred to as lost circulation).

During drilling, the drill bit breaks up the formation into smaller pieces referred to as drill cuttings. These drill cuttings affect the viscosity of the drilling fluid. Accordingly, the viscosity of the drilling fluid is measured often during drilling operations. Such measurements are typically not automated and complex, which decreases the accuracy of the measurements.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The embodiments described herein relate to in-line viscosity measurement systems and methods for measuring the viscosity of a fluid in a flow path. Such methods and apparatuses may be useful when integrated with drilling operations and systems for in-line measurement of drilling fluid viscosity.

The in-line viscosity measurement systems and methods described herein use oscillatory squeeze flow to determine the viscosity of a fluid between either two parallel plates or two coaxial surfaces to measure. The parallel plates or coaxial surfaces are disposed in a flow path (also referred to herein as a fluid flow path), which allows for the fluid between the parallel plates or coaxial surfaces to be exchanged for fresh fluid and provide on-demand and/or scheduled viscosity measurements. Further, the systems and methods described herein are automated, which provides for increased accuracy over the complex, non-automated methods presently employed.

Figure 1:
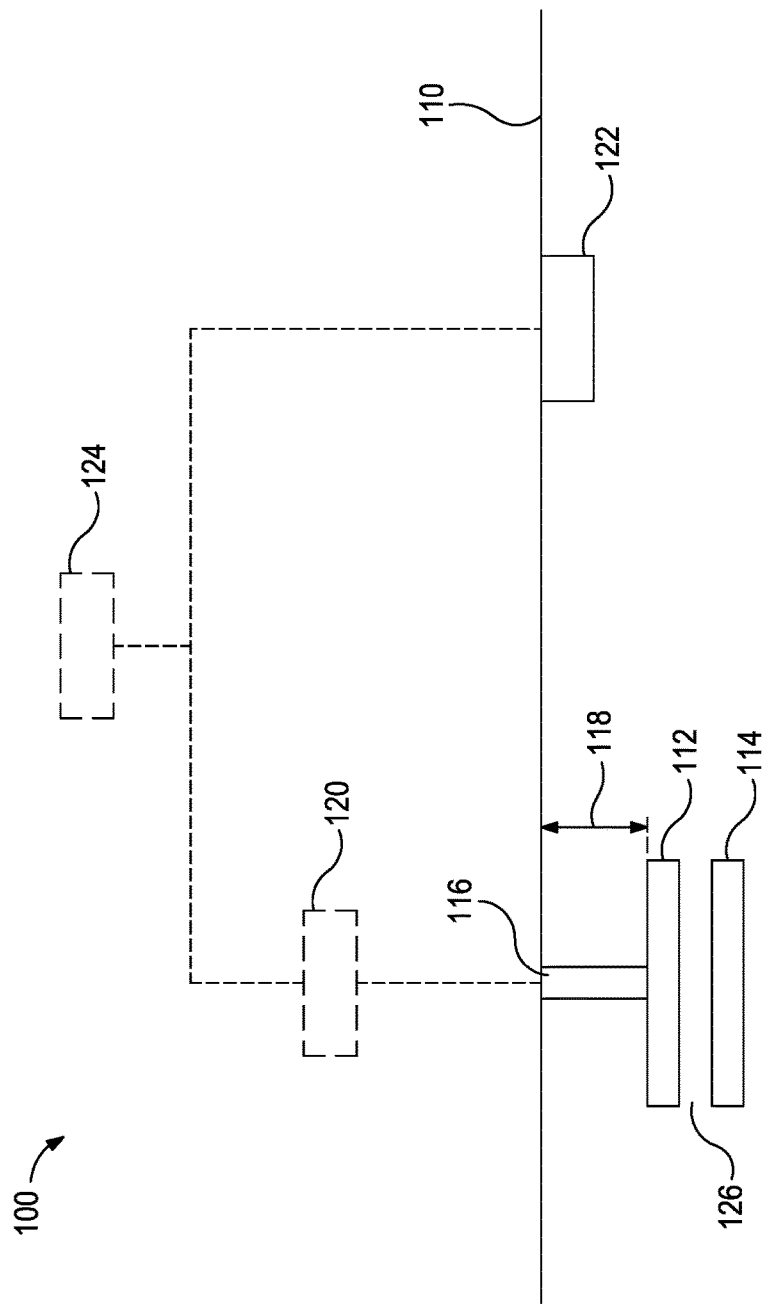
FIG. 1 provides a cross-sectional diagram of an in-line parallel plate system for measuring the viscosity of a fluid according to at least some embodiments described herein.

FIG. 1 provides a cross-sectional diagram of an in-line parallel plate system 100 for measuring the viscosity of a fluid according to at least some embodiments described herein. The system 100 includes a flow path 110 with two parallel plates 112,114 positioned therein. As fluid flows through the flow path 110, a portion of the fluid becomes disposed in the gap 126 between the two parallel plates. The first plate 112 is coupled to an actuator 116 configured to move the first plate 112 relative to the second plate 114 in an oscillatory motion according to a sine function illustrated by arrow 118, which is also referred to herein as a sine function oscillatory motion. The actuator 116 is coupled to a load cell 120 to determine the force applied to manipulate the first plate 112 in the sine function oscillatory motion relative to the second plate 114. Both the load cell 120 and a temperature sensor 122 in the flow path 110 are coupled to a processor 124 configured to receive the load measurements and temperature measurements, respectively, and calculate the viscosity of the fluid between the two parallel plates 112,114 according to an oscillatory squeeze flow regression.

An oscillatory squeeze flow regression relates the force applied to create the sine function oscillatory motion and the surface area of the parallel plates to the viscosity of the fluid. More specifically, the gap between the two parallel plates (h) can be represented as a function of the squeezing frequency ($\omega$) according to Equation 1, where $h_0$ is the gap 126 at an equilibrium position, $\varepsilon$ is the amplitude of the sine function, and t is time. Similarly, the total force (F) required to squeeze the two plates can be represented by Equation 2, where c is the phase angle between elastic and viscous components of the fluid and $F_0$ is the force at an equilibrium position.

$$h = h_0 + \varepsilon e^{i\omega t} \qquad \text{Equation 1}$$

$$F = F_0 + e^{i(\omega t + c)} \qquad \text{Equation 2}$$

With further derivation, Equations 3 and 4 can be derived for the storage moduli (G') and the loss moduli (G") of the fluid, where $\alpha$ is the diameter of the oscillating plate and $\rho$ is density (g/mL). It should be noted that for non-circular plates (e.g., square, rectangular, polygonal, or the like), the term $\alpha$ in Equations 3 and 4 may be replaced with $$a = \sqrt{\frac{4A}{\pi}},$$

where A is the surface area of the non-circular plates.

$$G' = \frac{2h^3 F_0 \cos(\omega c)}{3\pi\varepsilon a^4} + \frac{\omega^2 \rho h^2}{10} \qquad \text{Equation 3}$$

$$G'' = \frac{2h^3 F_0 \sin(\omega c)}{3\pi\varepsilon a^4} \qquad \text{Equation 4}$$

The viscosity ($\eta(\gamma)$) of the fluid, which is related to the dynamic viscosity ($\eta^*(\omega)$) can be obtained by Equation 5. Accordingly, Equation 5 may be used as the oscillatory squeeze flow regression for determining the viscosity of the fluid.

$$\eta(\gamma) = \eta*(\omega)|_{\omega=\gamma} = \sqrt{G'^2 + G''^2} \qquad \text{Equation 5}$$

Figure 2A:
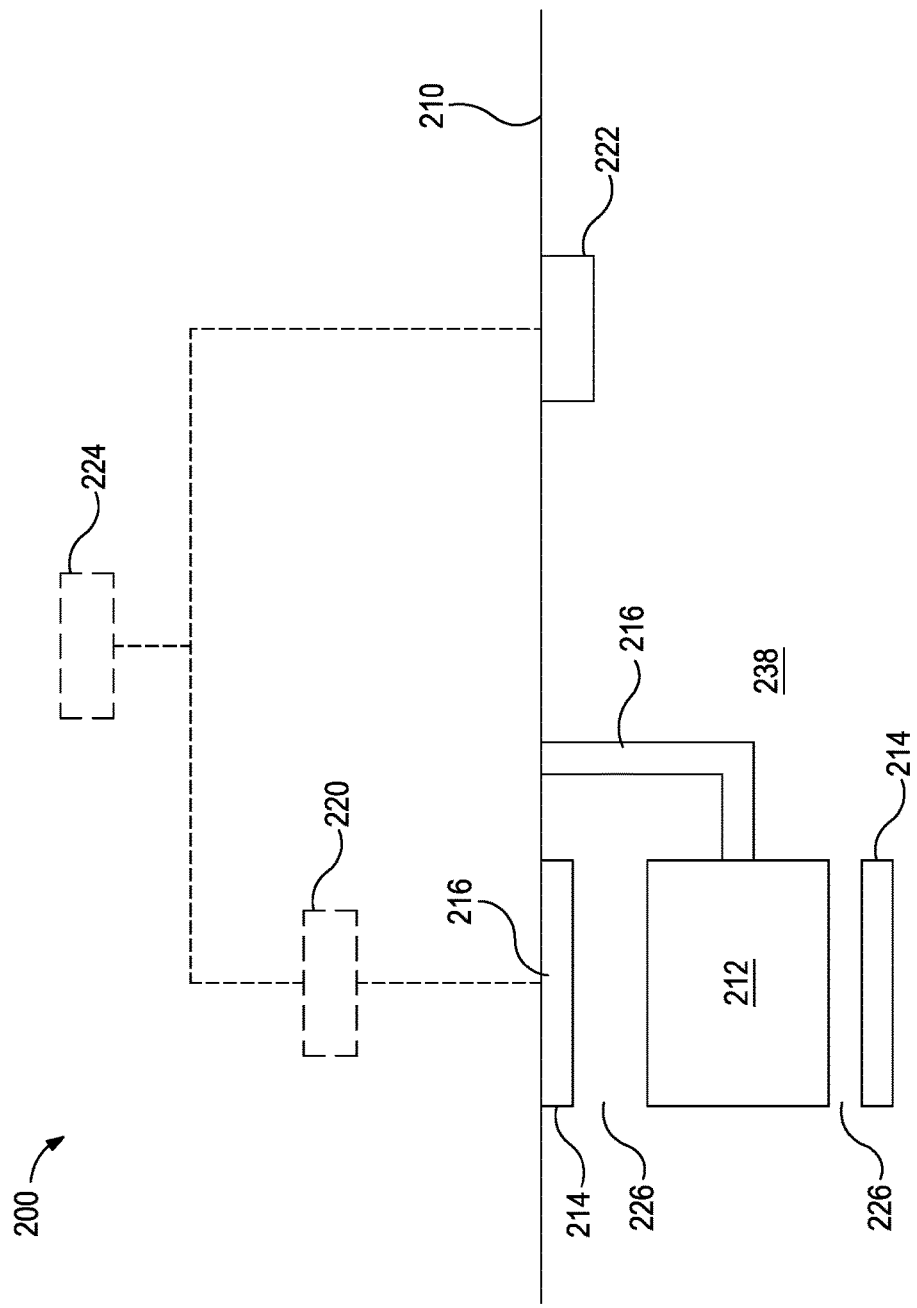
FIGS. 2A-2B provide a cross-sectional diagram and an end-on diagram, respectively, of an in-line coaxial system for measuring the viscosity of a fluid according to at least some embodiments described herein.
Figure 2B:
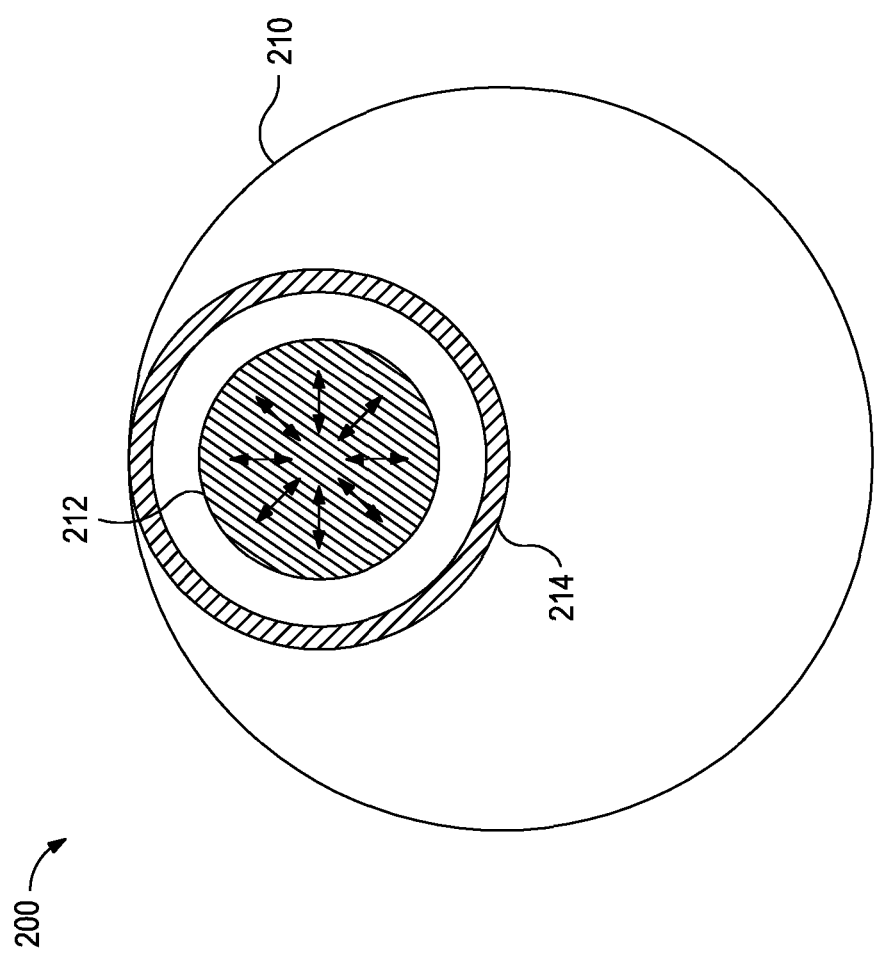

FIGS. 2A-2B provide a cross-sectional diagram and an end-on diagram, respectively, of an in-line coaxial system 200 for measuring the viscosity of a fluid according to at least some embodiments described herein. The system 200 includes a flow path 210 with two coaxial cylinders 212,214 positioned therein. As fluid flows through the flow path 210, a portion of the fluid becomes disposed in the gap 226 between the two coaxial cylinders 212,214. The inner cylinder 212 is coupled to an actuator 216 configured to move the inner cylinder 212 relative to the outer cylinder 214 radially according to the sine function oscillatory motion illustrated by arrows 218. For example, the inner cylinder 212 may be formed of an expandable material, and the actuator 216 may be a pneumatic device that uses air pressure to expand and contract the inner cylinder 212.

The actuator 216 is coupled to a load cell 220 to determine the force applied to manipulate the inner cylinder 212 in the sine function oscillatory motion relative to the outer cylinder 214. Both the load cell 220 and a temperature sensor 222 in the flow path 210 are coupled to a processor 224 configured to receive the load measurements and temperature measurements, respectively, and calculate the viscosity of the fluid between the two coaxial cylinders 212,214 according to an oscillatory squeeze flow regression (e.g., Equation 5). The additional surface area provided by the configuration of the two coaxial cylinders 212,214 may increase the resolution of the systems and methods described herein.

Figure 3:
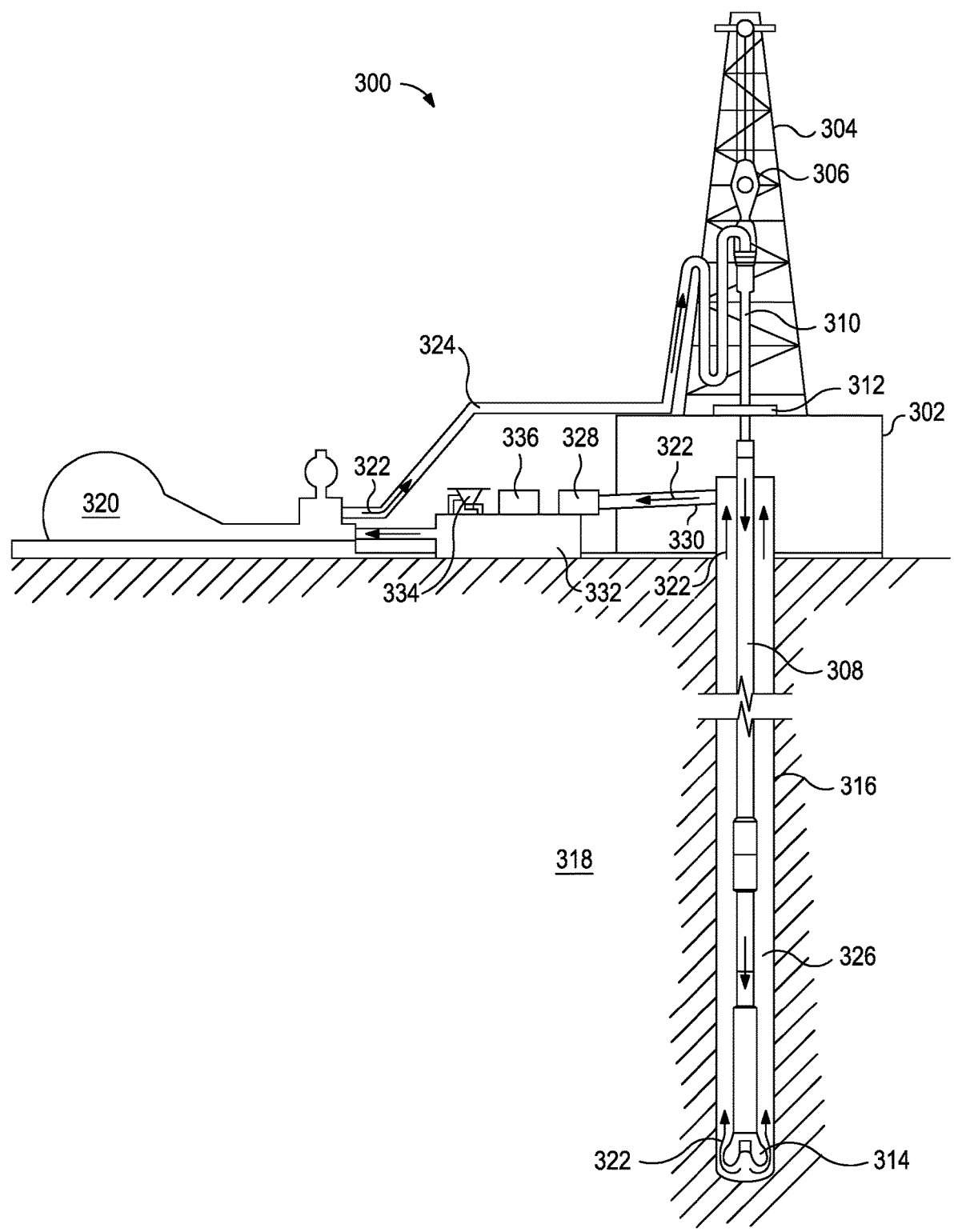
FIG. 3 provides a diagram of a drilling system that includes an in-line viscometer system according to at least some embodiments described herein.

FIG. 3 provides a diagram of a drilling system that includes an in-line viscometer system 336 (e.g., an in-line parallel system 100 or an in-line coaxial system 200) according to at least some embodiments described herein. It should be noted that while FIG. 3 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 300 may include a drilling platform 302 that supports a derrick 304 having a traveling block 306 for raising and lowering a drill string 308. The drill string 308 may include, but is not limited to, drill pipe and coiled tubing, as generally known to those skilled in the art. A kelly 310 supports the drill string 308 as it is lowered through a rotary table 312. A drill bit 314 is attached to the distal end of the drill string 308 and is driven either by a downhole motor and/or via rotation of the drill string 308 from the well surface. As the bit 314 rotates, it creates a wellbore 316 that penetrates various subterranean formations 318.

A pump 320 (e.g., a mud pump) circulates drilling fluid 322 through a feed pipe 324 and to the kelly 310, which conveys the drilling fluid 322 downhole through the interior of the drill string 308 and through one or more orifices in the drill bit 314. The drilling fluid 322 is then circulated back to the surface via an annulus 326 defined between the drill string 308 and the walls of the wellbore 316. At the surface, the recirculated or spent drilling fluid 322 exits the annulus 326 and may be conveyed to one or more fluid processing unit(s) 328 (e.g., shakers) via an interconnecting flow line 330. The one or more fluid processing unit(s) 328 may be useful in removing large drill cuttings that may interfere with the viscosity measurements described herein. After passing through the fluid processing unit(s) 328, a "cleaned" drilling fluid 322 is deposited into a nearby retention pit 332 (i.e., a mud pit). While illustrated as being arranged at the outlet of the wellbore 316 via the annulus 326, those skilled in the art will readily appreciate that the fluid processing unit(s) 328 may be arranged at any other location in the drilling assembly 300 to facilitate its proper function, without departing from the scope of the disclosure.

One or more additives (e.g., weighting agents) may be added to the drilling fluid 322 via a mixing hopper 334 communicably coupled to or otherwise in fluid communication with the retention pit 332. The mixing hopper 334 may include, but is not limited to, mixers and related mixing equipment known to those skilled in the art. In other embodiments, however, additives may be added to the drilling fluid 322 at any other location in the drilling assembly 300. In at least one embodiment, for example, there could be more than one retention pit 332, such as multiple retention pits 332 in series. Moreover, the retention pit 332 may be representative of one or more fluid storage facilities and/or units where additives may be stored, reconditioned, and/or regulated until added to the drilling fluid 322.

The drilling assembly 300 may include one or more in-line viscometer system 336 in fluid communication with the at least one retention pit 332. Samples of the drilling fluid in the retention pits 332 may be transported to the in-line viscometer system 336 to measure the viscosity of the drilling fluid 322. Further, based on the viscosity measurements, one or more additives may be added to the drilling fluid via the mixing hopper 332 to adjust the viscosity of the drilling fluid to a desired value.

While not specifically illustrated herein, the drilling assembly 300 may also include additional components, for example, shakers (e.g., shale shaker), centrifuges, hydrocyclones, separators (e.g., magnetic and electrical separators), desilters, desanders, filters (e.g., diatomaceous earth filters), heat exchangers, fluid reclamation equipment, sensors, gauges, pumps, compressors, conduits, pipelines, trucks, tubulars, pipes, pumps, compressors, motors, valves, floats, drill collars, mud motors, downhole motors, downhole pumps, MWD/LWD tools, tool seals, packers, roller cone bits, PDC bits, natural diamond bits, any hole openers, reamers, coring bits, and the like, and any communication components associated therewith (e.g., wirelines, telemetry components, etc.).

The systems described herein may be useful in measuring the viscosity of a drilling fluid while drilling a wellbore penetrating a subterranean formation and may allow for changing the viscosity of the drilling fluid during such an operation. For example, after removing the larger drill cuttings (e.g., 1 mm or larger) with shakers, centrifuges, or the like, the viscosity of the drilling fluid may be measured. Then, the viscosity of the drilling fluid may be increased or decreased to meet the requirements of the drilling operation. For example, weighting agents, viscosifiers, or the like may be added to increase viscosity, while a breaker, additional base fluid, or the like may be added to decrease the viscosity.

Embodiments disclosed herein include

Embodiment A: a method that includes drilling a wellbore penetrating a subterranean formation while circulating a drilling fluid through the wellbore; measuring the viscosity of the drilling fluid with an in-line viscometer systems after the drilling fluid has circulated through the wellbore, the in-line viscometer system comprising either: (1) a fluid flow path with two coaxial cylinders positioned therein to allow for a fluid flowing through the flow path to also flow between the two coaxial cylinders; an actuator configured to contract and expand at least one of the two coaxial cylinders and away from each other in a sine function oscillatory motion; a load cell coupled to one of the two parallel plates to measure a total force applied to the plate; a temperature sensor; and a processor for receiving temperature data from the temperature sensor and the total force applied from the load cell and calculating a viscosity of the fluid; (2) the fluid flow path with two parallel plates positioned therein to allow for the fluid flowing through the flow path to also flow between the two parallel plates; the actuator configured to move the two plates towards and away from each other in the sine function oscillatory motion; the load cell coupled to one of the two parallel plates to measure the total force applied to the plate; the temperature sensor; and the processor for receiving temperature data from the temperature sensor and the total force applied from the load cell and calculating the viscosity of the fluid; or (3) a combination thereof;

Embodiment B: a method that includes circulating a drilling fluid through a wellbore penetrating a subterranean formation while drilling the wellbore; passing the drilling fluid through two parallel plates, two coaxial cylinders, or both; moving at least one of the parallel plates, at least one of the two coaxial cylinders, or both to produce a sine function oscillatory motion between the two parallel plates, the two coaxial cylinders, or both; measuring a force required to produce the sine function oscillatory motion; and calculating a viscosity of the drilling fluid; and Embodiment C: a system that includes a line fluidly connecting a mixing tank and a tubular extending into a wellbore with a pump disposed along the line between the mixing tank and the tubular; one or more in-line viscometer systems in fluid communication with the line between the mixing tank and the pump, the one or more in-line viscometer systems comprising either: (1) a fluid flow path with two coaxial cylinders positioned therein to allow for a fluid flowing through the flow path to also flow between the two coaxial cylinders; an actuator configured to contract and expand at least one of the two coaxial cylinders and away from each other in a sine function oscillatory motion; a load cell coupled to one of the two parallel plates to measure a total force applied to the plate; a temperature sensor; and a processor for receiving temperature data from the temperature sensor and the total force applied from the load cell and calculating a viscosity of the fluid; (2) the fluid flow path with two parallel plates positioned therein to allow for the fluid flowing through the flow path to also flow between the two parallel plates; the actuator configured to move the two plates towards and away from each other in the sine function oscillatory motion; the load cell coupled to one of the two parallel plates to measure the total force applied to the plate; the temperature sensor; and the processor for receiving temperature data from the temperature sensor and the total force applied from the load cell and calculating the viscosity of the fluid; or (3) a combination thereof.

Each of Embodiments A and B may have one or more of the following additional elements in any combination: Element 1: the method further including removing at least some drill cuttings from the drilling fluid before measuring the viscosity of the drilling fluid or before passing the drilling fluid through the two parallel plates, the two coaxial cylinders, or both; Element 2: the method further including adding weighting agents to the drilling fluid after measuring the viscosity of the drilling fluid to increase the viscosity of the drilling fluid or before after calculating the viscosity of the drilling fluid to increase the viscosity of the drilling fluid; Element 3: the method further including adding a viscosifier to the drilling fluid after measuring the viscosity of the drilling fluid to increase the viscosity of the drilling fluid or after calculating the viscosity of the drilling fluid to increase the viscosity of the drilling fluid; Element 4: the method further including adding a breaker to the drilling fluid after measuring the viscosity of the drilling fluid to decrease the viscosity of the drilling fluid or after calculating the viscosity of the drilling fluid to decrease the viscosity of the drilling fluid; and Element 5: the method further including adding a base fluid to the drilling fluid after measuring the viscosity of the drilling fluid to decrease the viscosity of the drilling fluid or after calculating the viscosity of the drilling fluid to decrease the viscosity of the drilling fluid.

By way of non-limiting example, exemplary combinations applicable to Embodiments A and B include: Element 1 in combination with Element 2; Element 1 in combination with Element 3 and optionally Element 2; Element 1 in combination with Element 4; Element 1 in combination with Element 5 and optionally Element 4; Elements 2 and 3 in combination; and Elements 4 and 5 in combination.

Unless otherwise indicated, all numbers expressing quantities of ingredients, properties such as molecular weight, reaction conditions, and so forth, used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
   drilling a wellbore penetrating a subterranean formation while circulating a drilling fluid through the wellbore in a fluid flow path;
   measuring the viscosity of the drilling fluid with an in-line viscometer system after the drilling fluid has circulated through the wellbore, the in-line viscometer system disposed within the fluid flow path and comprising either:
      two coaxial cylinders positioned within the fluid flow path, the coaxial cylinders spaced apart by a gap to allow for a fluid flowing through the flow path to also flow between the two coaxial cylinders; an actuator configured to radially contract and expand at least one of the two coaxial cylinders relative to the other coaxial cylinder in a sine function oscillatory motion, wherein the sine function oscillatory motion is in a direction perpendicular to the direction of the fluid flow path; a load cell coupled to one of the two coaxial cylinders to measure a total force applied to thereto; a temperature sensor; and a processor for receiving temperature data from the temperature sensor and the total force applied from the load cell and calculating a viscosity of the fluid.

2. The method of claim 1 further comprising: removing at least some drill cuttings from the drilling fluid before measuring the viscosity of the drilling fluid.

3. The method of claim 1 further comprising: adding weighting agents to the drilling fluid after measuring the viscosity of the drilling fluid to increase the viscosity of the drilling fluid.

4. The method of claim 1 further comprising: adding a viscosifier to the drilling fluid after measuring the viscosity of the drilling fluid to increase the viscosity of the drilling fluid.

5. The method of claim 1 further comprising: adding a breaker to the drilling fluid after measuring the viscosity of the drilling fluid to decrease the viscosity of the drilling fluid.

6. The method of claim 1 further comprising: adding a base fluid to the drilling fluid after measuring the viscosity of the drilling fluid to decrease the viscosity of the drilling fluid.

7. A method comprising:
   circulating a drilling fluid through a wellbore penetrating a subterranean formation while drilling the wellbore;
   passing the drilling fluid through two coaxial cylinders;
   moving at least one of the two coaxial cylinders to produce a sine function oscillatory motion between the two coaxial cylinders, wherein the sine function oscillatory motion is in a direction perpendicular to the direction of the circulating fluid;
   measuring a force required to produce the sine function oscillatory motion; and calculating a viscosity of the drilling fluid.

8. The method of claim 7 further comprising: removing at least some drill cuttings from the drilling fluid before passing the drilling fluid through the two parallel plates, the two coaxial cylinders, or both.

9. The method of claim 7 further comprising: adding weighting agents to the drilling fluid after calculating the viscosity of the drilling fluid to increase the viscosity of the drilling fluid.

10. The method of claim 7 further comprising: adding a viscosifier to the drilling fluid after calculating the viscosity of the drilling fluid to increase the viscosity of the drilling fluid.

11. The method of claim 7 further comprising: adding a breaker to the drilling fluid after calculating the viscosity of the drilling fluid to decrease the viscosity of the drilling fluid.

12. The method of claim 7 further comprising: adding a base fluid to the drilling fluid after calculating the viscosity of the drilling fluid to decrease the viscosity of the drilling fluid.

* * * * *